(12) United States Patent
Kokuryo et al.

(10) Patent No.: US 6,590,662 B2
(45) Date of Patent: Jul. 8, 2003

(54) OBJECT SENSOR AND A WINDSHIELD WIPER CONTROLLER USING THE SAME

(75) Inventors: Kazuto Kokuryo, Shiga (JP); Shinji Nagao, Shiga (JP)

(73) Assignee: Nippon Sheet Glass Co., Ltd., Osaka (JP)

( * ) Notice: Subject to any disclaimer, the term of this patent is extended or adjusted under 35 U.S.C. 154(b) by 192 days.

(21) Appl. No.: 09/748,434

(22) Filed: Dec. 26, 2000

(65) Prior Publication Data

US 2001/0012106 A1 Aug. 9, 2001

(30) Foreign Application Priority Data

Dec. 28, 1999 (JP) .............................. 11-372504

(51) Int. Cl.[7] .............................................. G01N 21/55
(52) U.S. Cl. ..................... 356/445; 318/483; 250/573
(58) Field of Search ..................... 356/445; 250/214 R, 250/214 C, 214.1, 215, 573, 574; 318/483; 340/602; 327/514

(56) References Cited

U.S. PATENT DOCUMENTS 4,916,374 A    4/1990  Schierbeek et al.
5,225,669 A    7/1993  Hasch et al.

FOREIGN PATENT DOCUMENTS

| FR | 2787406 | 6/2002 |
| JP | 57-118952 | 7/1982 |
| JP | 2-68248 | 3/1990 |
| JP | 10-186059 | 7/1998 |

Primary Examiner—Richard A. Rosenberger
Assistant Examiner—Vincent P Barth
(74) Attorney, Agent, or Firm—Merchant & Gould P.C.

(57) ABSTRACT

An object sensor and object sensing method that sense the status of the sensing surface by detecting a dynamic impact of a rain drop, not by comparing the signal with a reference value. An object sensor sensing the status of a sensing surface by detecting a light with a photo detector, which light has been emitted by a photo emission element and reflected on the sensing surface, comprises: a means for generating a time lag signal from the output signal of the photo detector; a means for calculating a differential signal between the output signal of the photo detector and the time lag signal; and a means for judging the status of the sensing surface by detecting the generation of the differential signal.

60 Claims, 15 Drawing Sheets

| Input data | Data to be leveled | Shift-out data | Output data |
|---|---|---|---|
| Dn··· | [D8|D7|D6|D5|D4|D3|D2|D1] n | | → F(1) |
| Dn··· | [D9|D8|D7|D6|D5|D4|D3|D2] n | D1 | → F(2) |
| Dn··· | [D10|D9|D8|D7|D6|D5|D4|D3] n | D2 | → F(3) |

$F(1) = (D1 + D2 + \cdots + Dn) / n$ $F(2) = (D2 + D3 + \cdots + D(n+1)) / n$ $F(3) = (D3 + D4 + \cdots + D(n+2)) / n$

Fig.7

OBJECT SENSOR AND A WINDSHIELD WIPER CONTROLLER USING THE SAME

BACKGROUND OF THE INVENTION

1. Field of the Invention

The present invention relates to an object sensor and an object sensing method for sensing an object such as a water drop that exists on a sensing surface of a product. Especially, it is related to a rain sensor and a rain sensing method applied to vehicles, and a windshield wiper controller and a windshield wiper control method using the object sensor.

2. Description of the Related Art

Conventionally, many types of rain sensors for vehicles are developed. For example, a rain sensor employing an optical method as follows is known. A light emitted from a photo emission element (light emission element) is reflected on a sensing surface and the reflected light is received by a photo detector, and then a rain drop is sensed. That is, the reflection condition varies if an object such as a water drop exists on the sensing surface, and the amount of the detected light by the photo detector will decrease. A conventional rain sensor senses a rain drop by detecting this variation.

The above mentioned varying detection, normally, a method for comparison with the reference value (threshold method) had been used (i.e. JP 10-186059 A).

In practical use of such a conventional rain sensor, the rain sensor will be used in various conditions, so that a means for preventing malfunction is necessary. In order to achieve this object, the conventional rain sensor uses plural reference values which are set according to the operation modes (JP 10-186059 A), or replaces and switches reference values one by one (JP 2-68248 A).

As mentioned above, with the conventional rain sensor, the logic for rain drop detection is complicated, and consequently, a high-speed processing for of rain drop detection becomes difficult. In addition, in either of the above mentioned conventional methods, the rain drop is detected by the comparison with the reference value based on judging the status on the sensing surface. Therefore, the prevention of the malfunction is difficult because of the influence of the light from the outside or the influence of the status of the sensing surface, e.g. where dirt is present.

Moreover, the photo emission element and the photo detector have a disadvantage that the element characteristic will vary when the temperature varies. Especially, the photo emission element such as LED has a characteristic that the output will decrease when the temperature rises. By this characteristic, such element has a problem that an appropriate detection cannot be processed unless data correction by monitoring and feeding back the output is processed.

For example, in JP 57-118952 A, a windshield wiper controller is disclosed. This apparatus employs a method in which a light emitted from a photo emission element and reflected on the surface of a windshield glass is received by a photo detector, then the amount of the rain drop is judged according to the received light signal level, and the windshield wiper is driven.

In more detail, the received light signal is detected, then the detected signal is provided to the differential circuit and pulse signals corresponding to the envelope of the received light signal are picked out, and these pulse signals are counted.

In this JP 57-118952 A, the detailed method of how to pick out the pulse signals is not clearly disclosed. However, judging from FIG. 3(c) of the publication, the system will pick out a pulse signal when detecting the intersection of the envelope and the threshold.

In short, in the technology disclosed in the JP 57-118952 A, a rain drop impacting the surface of the windshield may be detected and counted and the detection for impact of a rain drop is processed by comparison the envelope with the threshold.

SUMMARY OF THE INVENTION

Therefore, with the foregoing in mind, the object of the present invention is not to judge the status of the sensing surface by comparison of the signal from the sensing surface with the reference value. The present invention provides an object sensor and a object sensing method that can detect the dynamic impact of a rain drop and does not require the complex judgment logic and also provides a windshield wiper controller using the object sensor.

Moreover, the object of the present invention is to provide an object sensor and a object sensing method that can detect a rain drop appropriately even though the signal level fluctuates and provide a windshield wiper controller using the object sensor.

In order to solve the above-mentioned problems, the first object sensor sensing the status of a sensing surface by detecting a light with a photo detector, which light has been emitted by a photo emission element and reflected on the sensing surface, comprises: a means for generating a time lag signal from the output signal of the photo detector; a means for calculating a differential signal between the output signal of the photo detector and the time lag signal; and a means for judging the status of the sensing surface by detecting the generation of the differential signal.

According to the above mentioned configuration, the status of the sensing surface can be detected by evaluating the variation over time of the signal level, not evaluating the signal level itself of the photo detector.

In order to solve the above-mentioned problems, the second object sensor sensing the status of a sensing surface by detecting a light with a photo detector, which light has been emitted by a photo emission element and reflected on the sensing surface, comprises: a means for canceling noise in a signal outputted from a photo detector; a means for generating a time lag signal from the noise-cancelled signal; a means for calculating a differential signal between the noise-cancelled signal and the time lag signal; and a means for judging the status of the sensing surface by detecting the generation of the differential signal.

According to the above configuration, the status of the sensing surface can be detected by evaluating the differential signal between the variation over time of the signal from the noise canceling processing and the variation over time of the first order time lag signal generated from the noise-cancelled signal, not by evaluating the signal level itself of the photo detector, so that the small fluctuation such as noise can be eliminated and only the significant varying of the signal level can be detected based on the status on the sensing surface.

In order to solve the above-mentioned problems, the third object sensor sensing the status of a sensing surface by detecting a light with a photo detector, which light has been emitted by a photo emission element and reflected on the sensing surface, comprises: a means for generating a first order time lag signal from the output signal of the photo detector; a means for generating a second order time lag signal from the first order time lag signal; a means for calculating a differential signal between the first order time lag signal and the second order time lag signal; and a means for judging the status of the sensing surface by detecting the generation of the differential signal.

According to the above configuration, the status of the sensing surface can be detected by evaluating the differential signal between the first order time lag signal and the second order time lag signal, not by evaluating the signal level itself of the photo detector. Because of evaluating the differential signal between the first order time lag signal and the second order time lag signal, the small fluctuation such as noise can be eliminated and only the significant varying of the signal level can be detected based on the status on the sensing surface.

It is preferable that in the above mentioned first, second or third object sensor, said means for canceling the noise and/or said means for generating a time lag signal are/is an analog circuit for generating the time lag signal.

It is preferable that the object sensor further comprises an A/D conversion means for converting an analog signal to a digital signal by sampling the analog signal of the photo detector by a predetermined period; wherein said means for canceling the noise and/or said means for generating a time lag signal are/is a means for leveling the predetermined number of the sampled signal inputted sequentially from the A/D conversion means.

According to the above configuration, a simple analog circuit element or a simple digital processor can be used as a means for canceling a noise signal or a means for generating a time lag signal, so that the circuit configuration becomes simple.

It is preferable that in the above mentioned first, second or third object sensor, the object to be sensed is the impact of a water drop on the sensing surface.

The object to be sensed is a water drop, so that the object sensor of this invention can be utilized as a water drop sensor for sensing the impact of a water drop on the sensing surface.

It is preferable that in the above mentioned first, second or third object sensor, wherein said object to be sensed is an impact of a water drop on the sensing surface, when the differential signal is calculated as a value by subtracting the signal of the photo detector or the signal of the noise-cancelled signal from the time lag signal, the impact of a water drop on the sensing surface is sensed when a positive differential signal is generated.

According to the above configuration, the differential signal is evaluated as a value by subtracting the signal of the photo detector or the noise-cancelled signal, and the impact of the water drop can be detected surely if the significant, positive differential signal which is generated between both signals in the part where the decrease of the signal level by the impact of the water drop is seen.

It is preferable that in the above mentioned third object sensor, wherein said object to be sensed is a impact of a water drop on the sensing surface, when the differential signal is calculated as a value by subtracting the first order time lag signal from the second order time lag signal, the impact of a water drop on the sensing surface is sensed when a positive differential signal is generated.

According to the above configuration, the differential signal is evaluated as a value by subtracting the first order time lag signal from the second order time lag signal, and the impact of the water drop can be detected surely if the significant, positive differential signal, which is generated between both signals in the part where the decrease of the signal level by the impact of the water drop, is seen.

It is preferable that the size of the water drop impacting the sensing surface is judged by the value of the differential signal. This becomes possible because the larger the size of a water drop, the bigger the level of the decrease of the signal level of the photo detector caused by impact of the water drop on the sensing surface.

It is preferable that the spike noise is cancelled precedingly from the signal of the photo detector.

In the above mentioned description, an object to be sensed is assumed to be a water drop, in addition, a water drop is assumed as a rain drop, the object sensor can sense whether it is raining or not.

A windshield wiper control system of the present invention controls a windshield wiper operation by the signal outputted from the object sensor of the above mentioned present invention.

According to the above configuration, the windshield wiper control system can sense a rain drop with high accuracy and perform windshield wiper operation control automatically.

In order to solve the above-mentioned problems, the first object sensing method of the present invention for sensing the status of a sensing surface by detecting a light with a photo detector, which light has been emitted by a photo emission element and reflected on the sensing surface, comprises: generating a time lag signal from the output signal of the photo detector; calculating a differential signal between the output signal of the photo detector and the time lag signal; and judging the status of the sensing surface by detecting the generation of the differential signal.

In order to solve the above-mentioned problems, the second object sensing method of the present invention for sensing the status of a sensing surface by detecting a light with a photo detector, which light has been emitted by a photo emission element and reflected on the sensing surface, comprises: canceling a noise in a signal outputted from a photo detector; generating a time lag signal from the noise-cancelled signal; a circuit element for calculating a differential signal between the noise-cancelled signal and the time lag signal; and judging the status of the sensing surface by detecting the generation of the differential signal.

In order to solve the above-mentioned problems, the third object sensing method of the present invention for sensing the status of a sensing surface by detecting a light with a photo detector, which light has been emitted by a photo emission element and reflected on the sensing surface, comprises: generating a first order time lag signal from the output signal of the photo detector; generating a second order time lag signal from the first order time lag signal; calculating a differential signal between the first order time lag signal and the second order time lag signal; and judging the status of the sensing surface by detecting the generation of the differential signal.

These and other advantages of the present invention will become apparent to those skilled in the art upon reading and understanding the following detailed description with reference to the accompanying figures.

BRIEF DESCRIPTION OF THE DRAWINGS

FIG. 7 is a schematic diagram showing the data processing operated in a digital filter.

DESCRIPTION OF THE PREFERRED EMBODIMENTS

The object sensor and object sensing method according to the present invention will be described by way of illustrative embodiments.

The feature of this invention is sensing a dynamic water drop impact on the sensing surface. On the other hand, the conventional rain sensor senses a static rain drop present on the sensing surface by detecting the status on the sensing surface by comparison with the reference value.

This invention achieves dynamic object sensing by detailed study of comparing the dynamic status varying by a dynamic rain drop impact on the sensing surface and the static status when a rain drop exists statically on the sensing surface.

(Measurement Principle)

Figure 1:
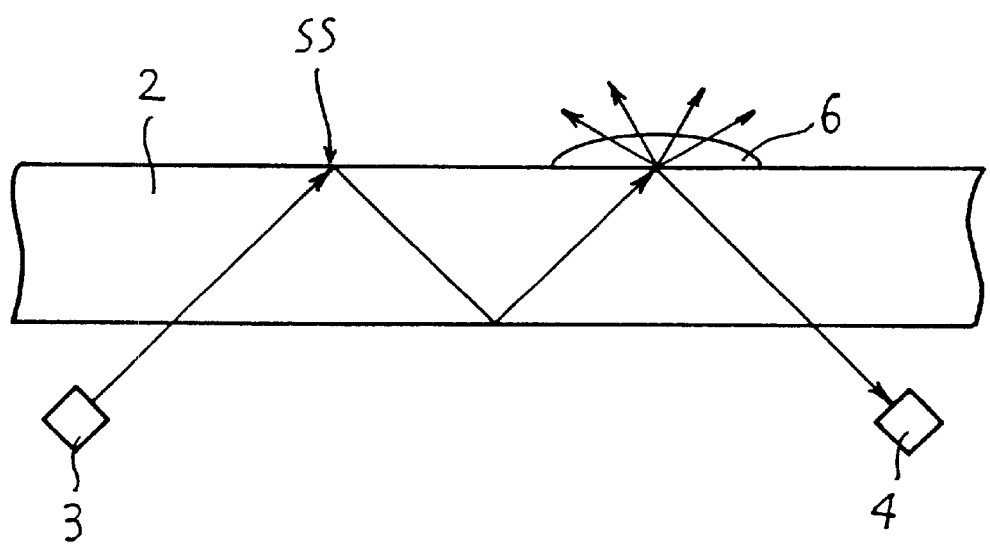
FIG. 1 is a schematic diagram showing a basic principle of an optical system employed in an object sensor of this invention.

First, a basic principle of the optical system employed in the object sensor is described by referencing FIG. 1. For, example, as shown in FIG. 1, a light emitted from the photo emission element (3) such as LED is led to the transparent glass sheet (2) on which surface a water drop will be sensed. The led light causes a total reflection on the sensing surface, and for instance, the reflected light is received by the photo detector (4) such as a photo diode. The photo detector (4) is installed in the object sensor so that the output signal becomes maximum when no water drop exists on the sensing surface. Therefore, if there is a water drop present on the sensing surface, the output signal level of the photo detector will be decreased because of variation in the reflection condition at the sensing surface. The object sensor of this invention detects the decease of the output signal level and judges the dynamic water drop impacting the sensing surface.

Figure 2:
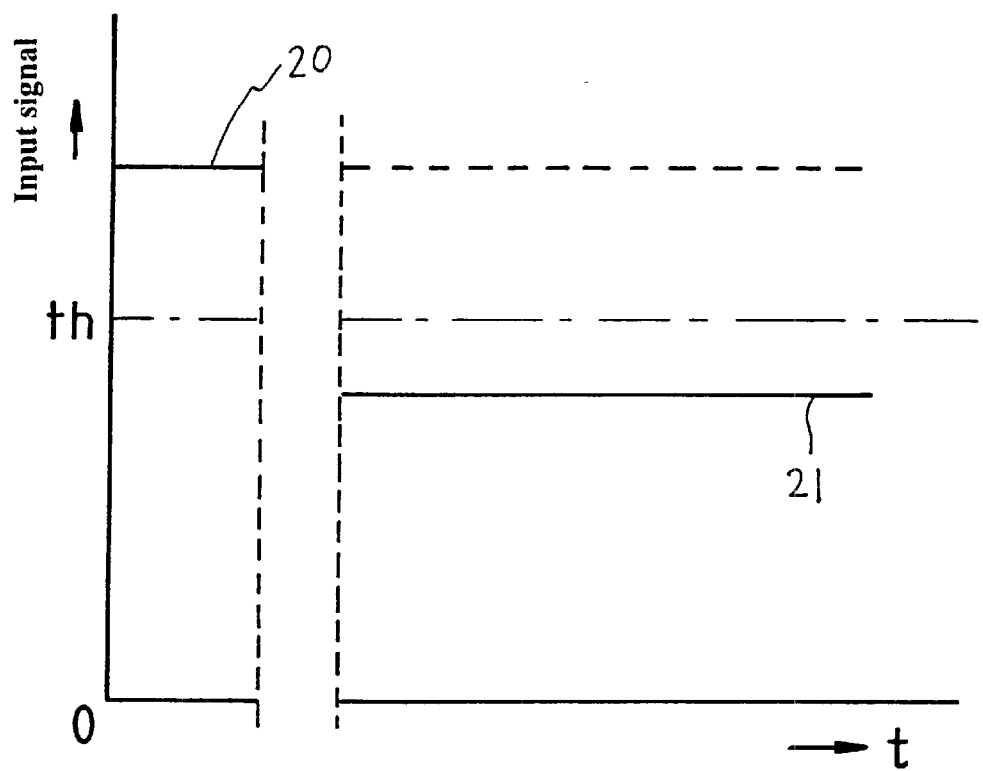
FIG. 2 is a schematic diagram showing the signal model of the photo detector and the decrease of the signal level in the case that a water drop is present on the sensing surface statically.

FIG. 2 shows the input signal model inputted from the photo detector in the case that a water drop exists on the sensing surface statically and in the case that no water drop exists on the sensing surface. The signal level (20) shows the case where no water drop exists on the sensing surface. On the other hand, the signal level (21) shows the case where a water drop exists on the sensing surface. The vertical axis indicates the value of the input signal, and the horizontal axis indicates the time base.

In case that a water drop exists on the sensing surface statically and the status of the water drop does not vary, there will be no varying in the signal level of the photo detector. Therefore, the time lag signal of this signal level is not generated. Of course, the differential value between the input signal and the time lag signal is not generated. In this case, when the signal level becomes lower than the appropriately preset threshold (th), the object sensor may judge the existence of a water drop.

FIG. 3(a) shows an example of the input signal model in the case that a water drop is impacting on the sensing surface dynamically. The output signal of the photo detector is inputted (shown as $D_{IN}$). The signal of the time lag element (F1) can be generated from this input signal ($D_{IN}$). Furthermore, the differential signal ($\Delta(F1-D_{IN})$) calculated by subtracting the above mentioned input signal ($D_{IN}$) from the above-mentioned time lag signal (F1) can be generated. FIG. 3(b) shows an example of the generated differential signal model. In the differential signal ($\Delta(F1-D_{IN})$), a positive difference is generated between t0 and t1, and a negative difference is generated between t1 and t3.

Figure 3:
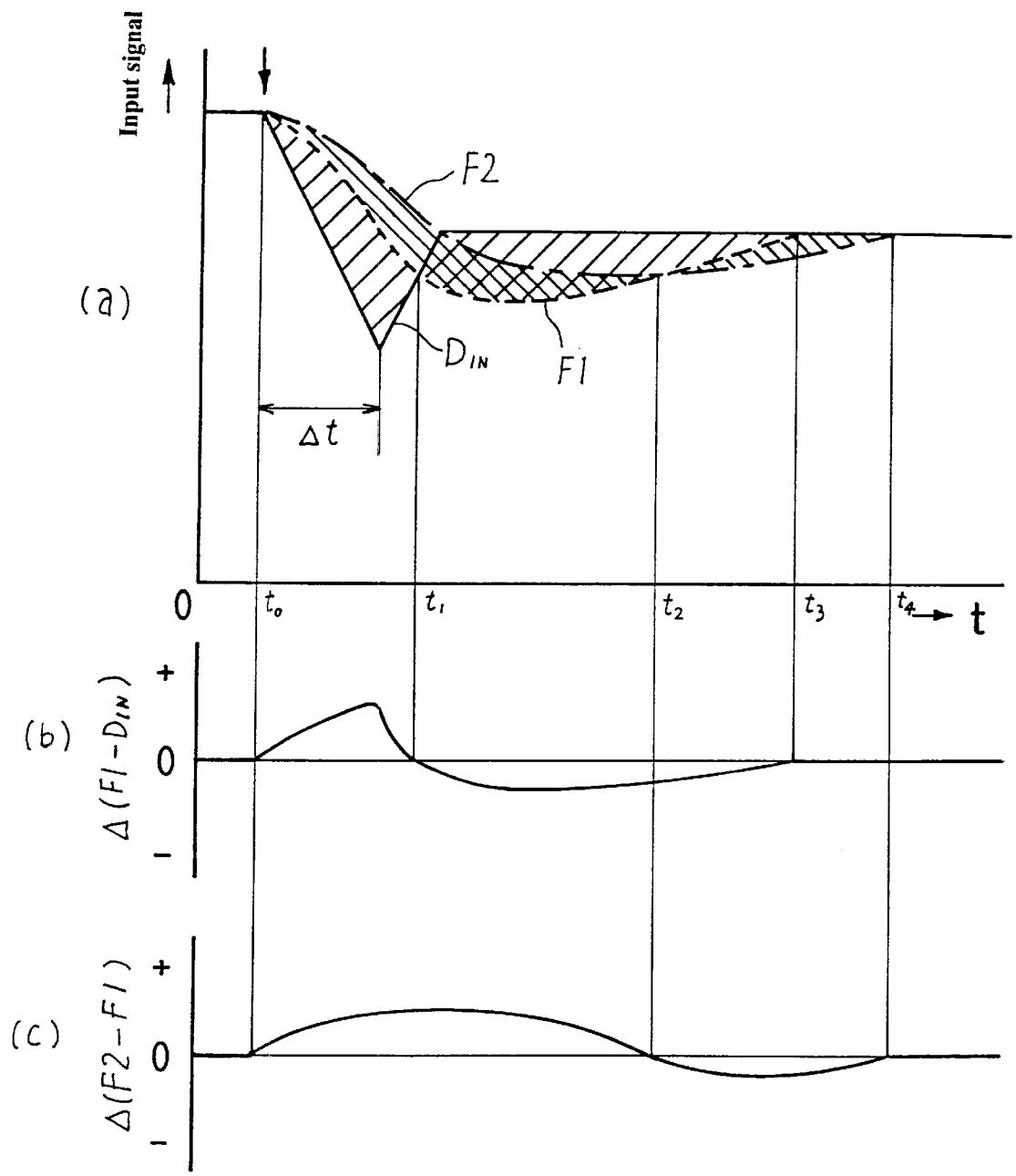
FIG. 3 is a schematic diagram showing a basic principle of the measurement method of this invention.

In FIG. 3(a), a water drop begins to impact the sensing surface at the time (t0) where the arrow indicates, and a period indicated by Δt corresponds to the situation that the water drop is collapsing. The subsequent signal part of a smooth level corresponds to a signal model showing the situation in which the water drop has collapsed and extended. When comparing the signal detected in case that a water drop exists on the sensing surface statically and the signal detected in case that a water drop impacting the sensing surface dynamically, it is understood that the differential signal shown as FIG. 3 has been generated in the latter case but not in the former case. In short, a water drop impacting on the sensing surface can be detected by detecting the generated differential signal. When the above mentioned differential signal is defined as a value ($\Delta(F1-D_{IN})$) calculated by subtracting the above mentioned input signal ($D_{IN}$) from the above-mentioned time lag signal (F1), if the above mentioned differential signal is positive, the object sensor can detect the fact that a water drop has impacted the sensing surface. If a dynamic water drop that impacts the sensing surface dynamically can be detected, the dynamic control of the windshield operation corresponding to the result of the sense of the dynamic water drop can become possible by counting the number of the water drops impacting the sensing surface. In both of the above mentioned cases, a water drop exists on the sensing surface. Therefore, the conventional rain sensor using a conventional threshold method (which compares the input signal value with the reference values) will sense a water drop as same in either case.

The problem of the conventional rain sensor is that if the size of a water drop that exists on the sensing surface is small, the decrease of the signal level inputted from the photo detector becomes small. Therefore, the conventional threshold method can not set such small threshold value appropriately because such small value is the same level as noise. That is, if the size of a water drop present on the sensing surface is small, the water drop can not be sensed by the conventional threshold method. On the contrary, the present invention can sense a rain drop impacting the sensing surface dynamically, and a rain drop can be sensed adequately even though a rain drop to be sensed is small and the signal level is difficult to be distinguished from the noise level. In short, even though the water drop is small, the windshield wiper controller can drive the wiper arm adequately when the windshield is to be cleared. Therefore, the case where a malfunction may happen can be reduced by applying the present invention. Here, the "malfunction" of the windshield wiper using the rain sensor means the case where a necessary operation is not carried out at the necessary time or an unnecessary operation is operated at an unnecessary time.

As explained above, in the water drop sensing method of the present invention, a varying of the status of the sensing surface is detected as a differential variation of the signal level. On the other hand, in the conventional threshold value method, a varying of the status of the sensing surface is detected as an integrated variation. Therefore, the water drop sensing method of the present invention can detect a fine varying of the status of the sensing surface.

In the above mentioned description, the object sensor senses a water drop by detecting the generation of the differential signal ($\Delta(F1-D_{IN})$) calculated by subtracting the input signal ($D_{IN}$) from the time lag signal (F1).

Furthermore, it is preferable that the object sensor generates a second order time lag signal (F2) from a first order time lag signal (F1), and generates the differential signal ($\Delta(F2-F1)$) calculated by subtracting the second order time lag signal (F2) from the first order time lag signal (F1), and senses a water drop by detecting the generated differential signal ($\Delta(F2-F1)$) (FIG. 3(c) is to be referenced).

The reason of the advantage of the above mentioned processing is as follows. The A/D converted input signal includes the quantization noise, and the pattern processing using the differential signal is suitable for detecting the fine difference but is weak as to the noise in general. In the differential signal ($\Delta(F2-F1)$), a positive difference is generated between t0 and t2, and a negative difference is generated between t2 and t4.

Next, specific examples of an object sensor and an object sensing method employing the above mentioned basic principle are shown as Embodiments below.

Embodiment 1

Following is the description of the object sensor of Embodiment 1 of this invention.

Figure 4:
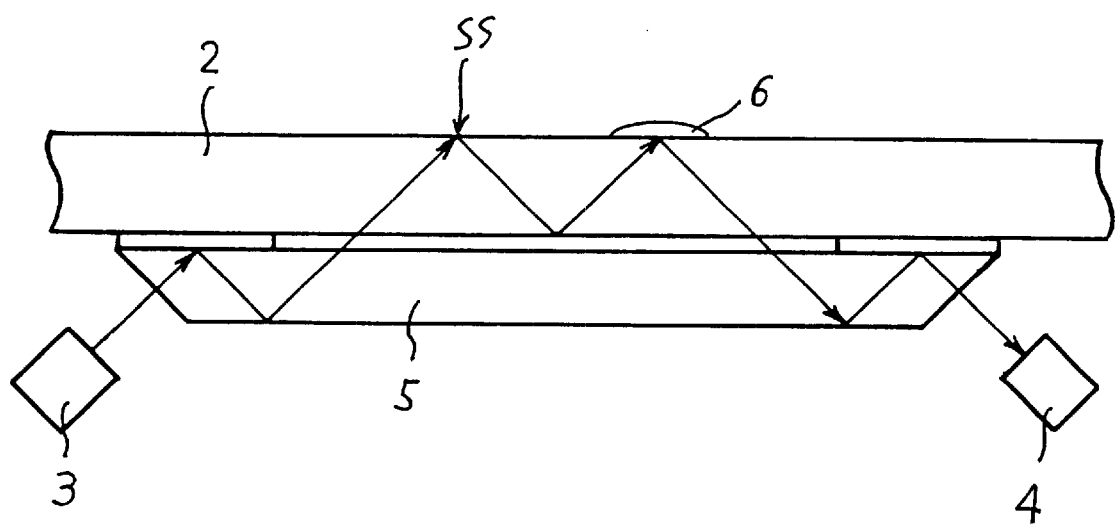
FIG. 4 is a schematic diagram showing a basic configuration of the optical system that can be applied to the object sensor of this invention.
Figure 5:
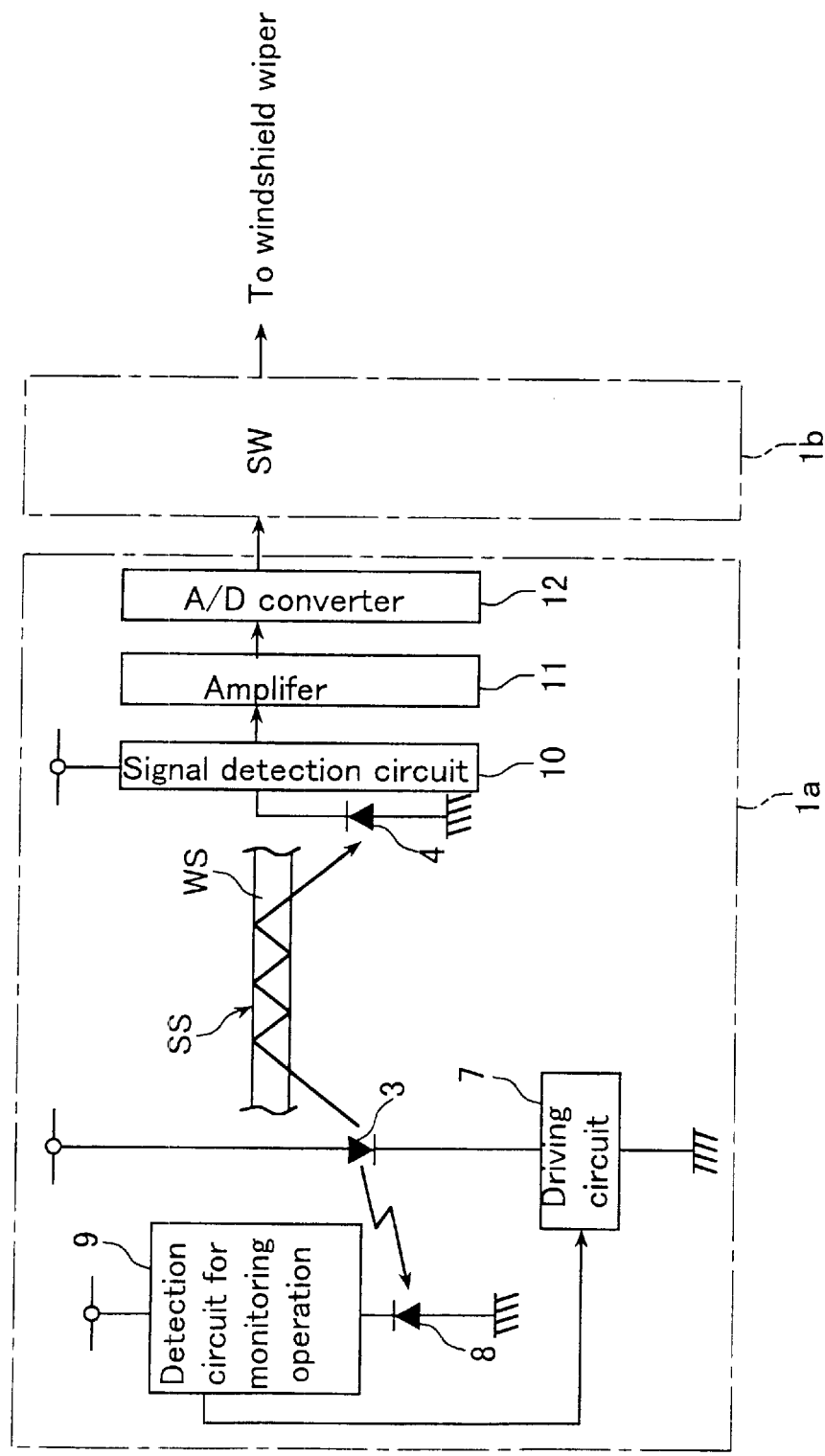
FIG. 5 is a block diagram showing the configuration of the hardware of the object sensor of Embodiment 1 of this invention.
Figure 6:
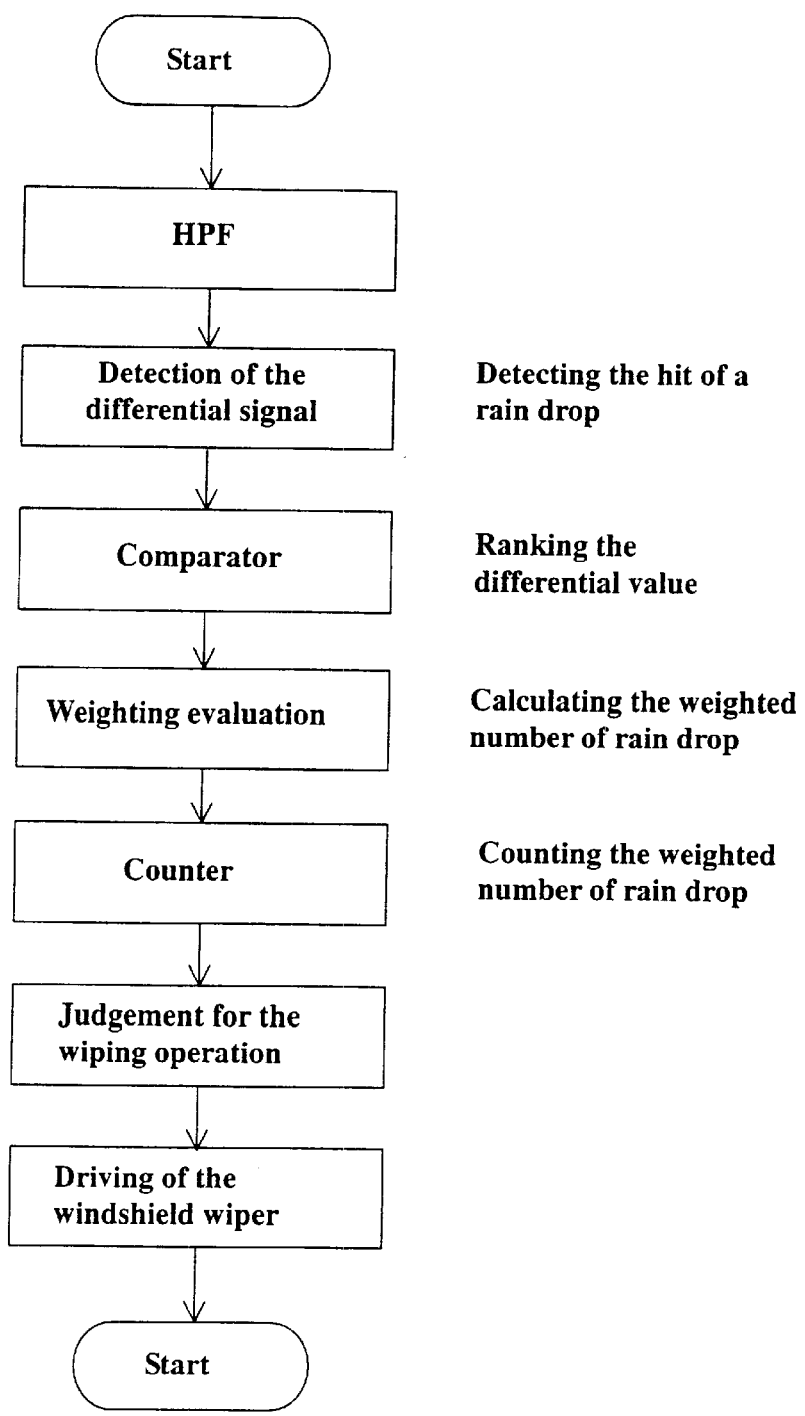
FIG. 6 is a flowchart showing the object sensing operations of this object sensor of this invention and windshield wiper driving operations of this invention.

First, the optical system employed in this Embodiment 1 is described by referencing the Figures. FIG. 4 is a diagram showing a basic configuration of the optical system applied to the object sensor of this Embodiment 1. FIG. 5 is a block diagram showing the configuration of the hardware of the object sensor of Embodiment 1 of this invention. FIG. 6 is a flowchart showing the object sensing operations of this object sensor of this Embodiment 1.

For, example, as shown in FIG. 4, a light emitted from the photo emission element (3) such as LED is led to the transparent glass sheet (2) on whose surface a water drop will be sensed. The led light causes a total reflection on the sensing surface (SS), and for instance, the reflected light is received by the photo detector (4) such as a photo diode via prism glass (5). In the object sensor shown in this Figure, the photo detector (4) is installed so that the output signal becomes maximum when there is no water drop present on the sensing surface (SS). Therefore, if there is a water drop (6) on the sensing surface (SS), the output signal level of the photo detector will be decreased because of variation of the reflection condition at the sensing surface. The photo emission element may be driven by a carrier pulse whose frequency (carrier frequency) is 500 Hz or more. It is preferable that the actual amount of the light emitted from the photo emission element (3) is monitored by a photo detector (8) for monitoring the operation and a circuit module (9) for monitoring the operation of the photo emission element because of the temperature characteristics of the photo emission element (3). It is preferable to drive the photo emission element (3) by the driving circuit (7) while feeding back the monitoring result (FIG. 5).

As shown in FIG. 5, the object sensor comprises a hardware module (1a) as a former section and a software module (1b) as a latter section. When the light is received in the photo detector (4) in the hardware module (1a) in the former section, the output signal is generated. At this moment, the detected signal includes carrier pulses used for driving the photo emission element, so that a significant real signal is taken out by the signal detector (10). It is preferable that the signal outputted from the photo detector (4) is amplified by the amplifier (11) because it is normally difficult to obtain a large volume signal outputted by the photo detector available in commercial use. Continuously, the amplified signal is inputted to the A/D converter (12), and converted into digital data. At this time, the dynamic range of the A/D converter (12) can be properly set according to the output signal of the optical system mentioned above.

Next, the water drop sensing operation logic employed in the object sensor of the present invention is described (FIG. 6 is to be referenced). It is preferable that the output of the A/D converter (12) is previously inputted into a noise canceling filter in order to cancel the spike noises generated by an irregular light coming from inside or outside of the car. This noise canceling processing also can be performed with software.

[LPF1]: Removal of Quantization Noise

First of all, the output of the noise canceling filter is inputted to the first digital filter such as low pass filter (LPF1). This LPF1 is used for eliminating the quantization noise generated in the digital conversion at the A/D converter (12) and canceling the noise generated in the other circuit modules used in the former stage. The output (F1) from the LPF1 can be understood as the first order time lag signal from the input signal ($D_{IN}$). The noise canceling processing in this LPF1 is performed as follows. Calculate the total value of the predetermined number of the sampling signal inputted sequentially and level with the number of samples. On this LPF1, the above mentioned predetermined number of samples is determined so as to cancel the spike noises to some extent.

The above mentioned predetermined number of samples is determined as follows. Measure the maximum noise level which can be assumed in this circuit and set the digital value corresponding to the maximum noise level. The above mentioned predetermined number of samples is determined as to eliminate the maximum level noise, in short, the number is determined as the value calculated by leveling the digital value with the number of samples so as to become "0". Normal level noise can be eliminated by leveling the input value sequentially. It is preferable that the data processing by this invention does not perform the floating point processing and omits decimals for high-speed processing.

By referring to FIG. 7, the level processing is described in detail. It is assumed that there is input data D(n) and data cells used in leveling processing. For example, when the sample number to be leveled is assumed as "8", 8 data cells are used and data D1 to D8 fetched from D(n) are inputted to data cells sequentially. The total number of these 8 data is leveled with the sample number "8" and the leveled value (F(1)) is outputted. Next, the data D9 is inputted to a data cell and the data D1 is shifted out in turn. In the same way as shown above, the total number of current 8 data is leveled with the sample number "8" and the leveled value (F(2)) is outputted. The leveling processing is performed in the same way.

[LPF2]: Generation of Time Lag Signal

The quantization noise-cancelled signal (F1) is inputted to the second digital filter such as low pass filter (LPF2). This LPF2 levels the total number of samples of the predetermined signal inputted sequentially with the number of samples the same as the LPF1. The time lag signal (F2) can be generated from the signal (F1) by the leveling process as mentioned above. The output signal (F2) from the LPF2 can be understood as the second order time lag signal from the input signal ($D_{IN}$). Two stage filtering mentioned above can be understood as a low pass filter which cuts the high frequency component. This process can be achieved in the analog circuit as described later.

[HPF]: Generation of Differential Signal

The output signal of the above mentioned LPF1 and the output signal of the above mentioned LPF2 are inputted to the third digital filter such as high pass filter (HPF3). The differential signal is generated by calculating the difference between the above-mentioned signal F1 and the signal F2. For instance, signal F1 is subtracted from the signal F2. The filtering processing for generating the differential value can be understood as a high pass filter, which extracts the high frequency component from the differential signal between the above-mentioned signal F1 and the signal F2.

[Detection of Differential Signal]: Detection of Dynamic Impact of an Object

A dynamic impact of an object such as a water drop can be sensed by detecting the differential signal generation. For instance, when the differential signal is assumed to be a value calculated by subtracting the signal F1 from the signal F2, and if the above mentioned difference value is positive, it can be assumed that the impact of the object such as a water drop on the sensing surface has happened. Oppositely, when the differential signal is assumed to be a value calculated by subtracting the signal F2 from the signal F1, and if the above mentioned difference value is negative, it can be assumed that the impact of the object such as a water drop on the sensing surface has happened.

The differential signal detection of the object sensor in an example of a configuration using the following elements is described. The optical system shown in FIG. 4 was used, and the photo detector and photo emission element as shown were used.

Photo emission element: LED; Made by Kyoto Semiconductor, KED352RHA

Photo detector: PD; Made by Kyoto Semiconductor, KPD4503K

In addition, the current/voltage conversion is carried out on the output of the photo detector by the following IC and it is amplified. The A/D conversion is carried out by the A/D converter built in the CPU. The A/D converted signal is inputted to the CPU and the software processing mentioned above is carried out on the signal.

The current/voltage converter and amplifier: Made by NEC; μ PC844

CPU: Made by Hitachi; H8S/2134 (A/D converter built in)

The canceling of the quantization noise (the first order time lag signal (LPF1)) is processed by leveling 8 data (n=8), and the generation of the time lag signal (the second order time lag signal (LPF2)) is conducted by leveling 4 data (n=4). The reason that the number of data in LPF2 is less than that of LPF1 is that the noise already has been cancelled by LPF1.

Figure 8:
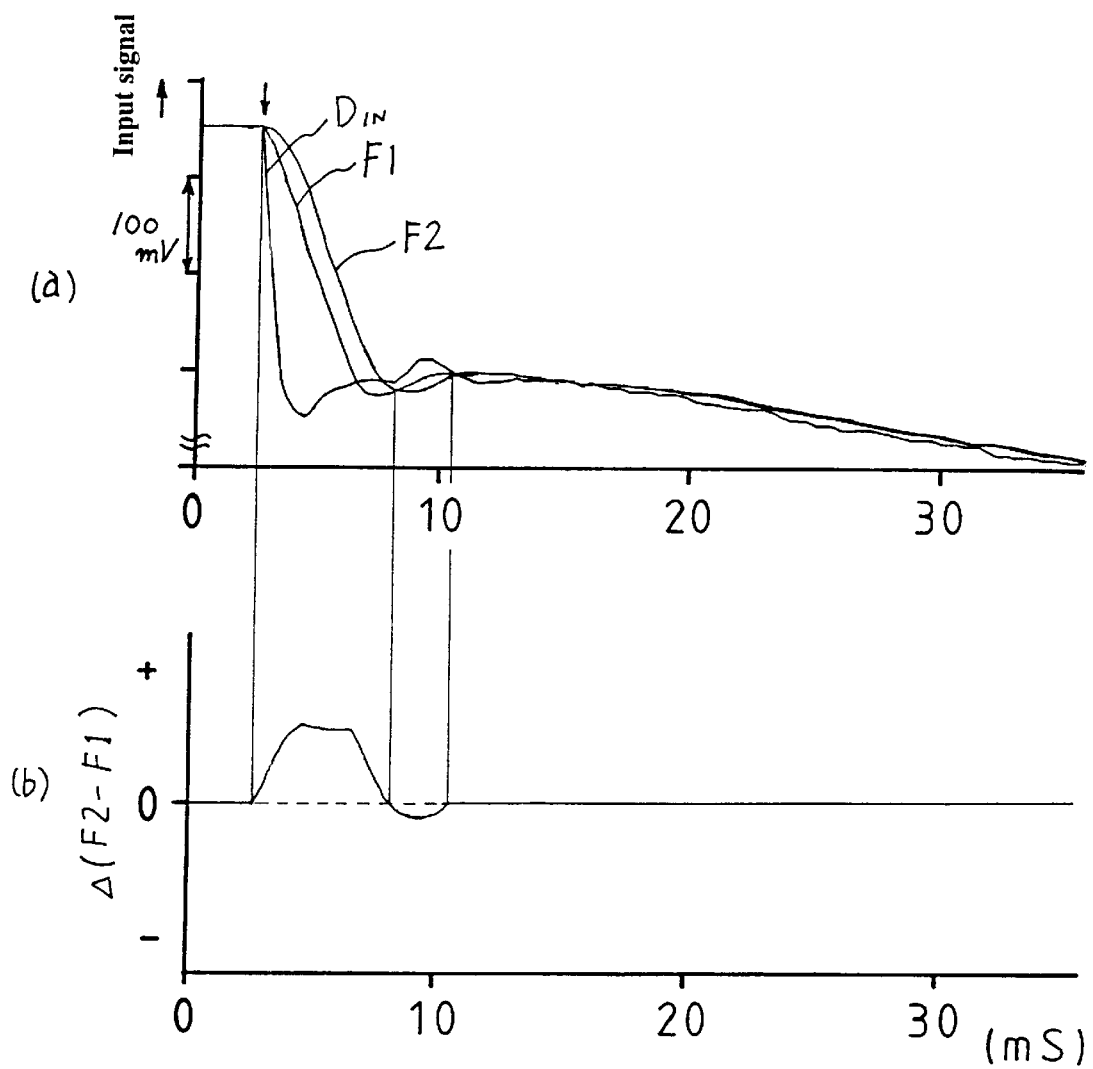
FIG. 8 is a schematic diagram showing the signal level of the photo detector and the processed signal level when a rain drop impacts the sensing surface.

FIG. 8 is a diagram showing an actual example of the signal level of the photo detector and the processed signal level where a rain drop impacts the sensing surface.

The graph FIG. 8(a) shows the actual input signal ($D_{IN}$), the noise-cancelled first order time lag signal (F1) and the second order time lag signal (F2). The graph FIG. 8(b) shows the differential signal calculated by subtracting signal F1 from signal F2. The horizontal axis is a time base. The rain drop began to impact the sensing surface at the timing of the arrow (↓) shown in the figure. It is clearly understood from FIG. 8 that a positive differential signal (Δ(F2−F1)) had been generated corresponding to the impact of the rain drop.

In addition, the following can be confirmed by the result shown in FIG. 8. That is, when generating the time lag signal (F2) from the noise-cancelled signal (F1), the time lag signal will become large when the signal F1 varies rapidly, and on the contrary, the time lag signal will become small when the signal F1 does not vary so much. In addition, when generating the differential signal between signal F2 and signal F1 (Δ(F2−F1(F1))), the differential signal will be enhanced and become large when the signal F1 varies rapidly, and on the contrary, the differential signal will not be generated when the signal F1 does not vary so much. Moreover, for instance, when the output of the photo emission element shifts slowly, the output of the photo detector also shifts. In this case, the accurate detection by the conventional rain drop sensing method using the fixed threshold value is difficult as described in the prior art. Therefore, the complex judgment logic should be required in the conventional method. On the contrary, with the object sensing method of the present invention using the detection of the differential signal of the first order time lag signal (F1) and the second order time lag signal (F2), the amount of the shift can be cancelled by taking the differential value, so that an appropriate rain drop sensing corresponding to the rain drop impact becomes possible.

Figure 9:
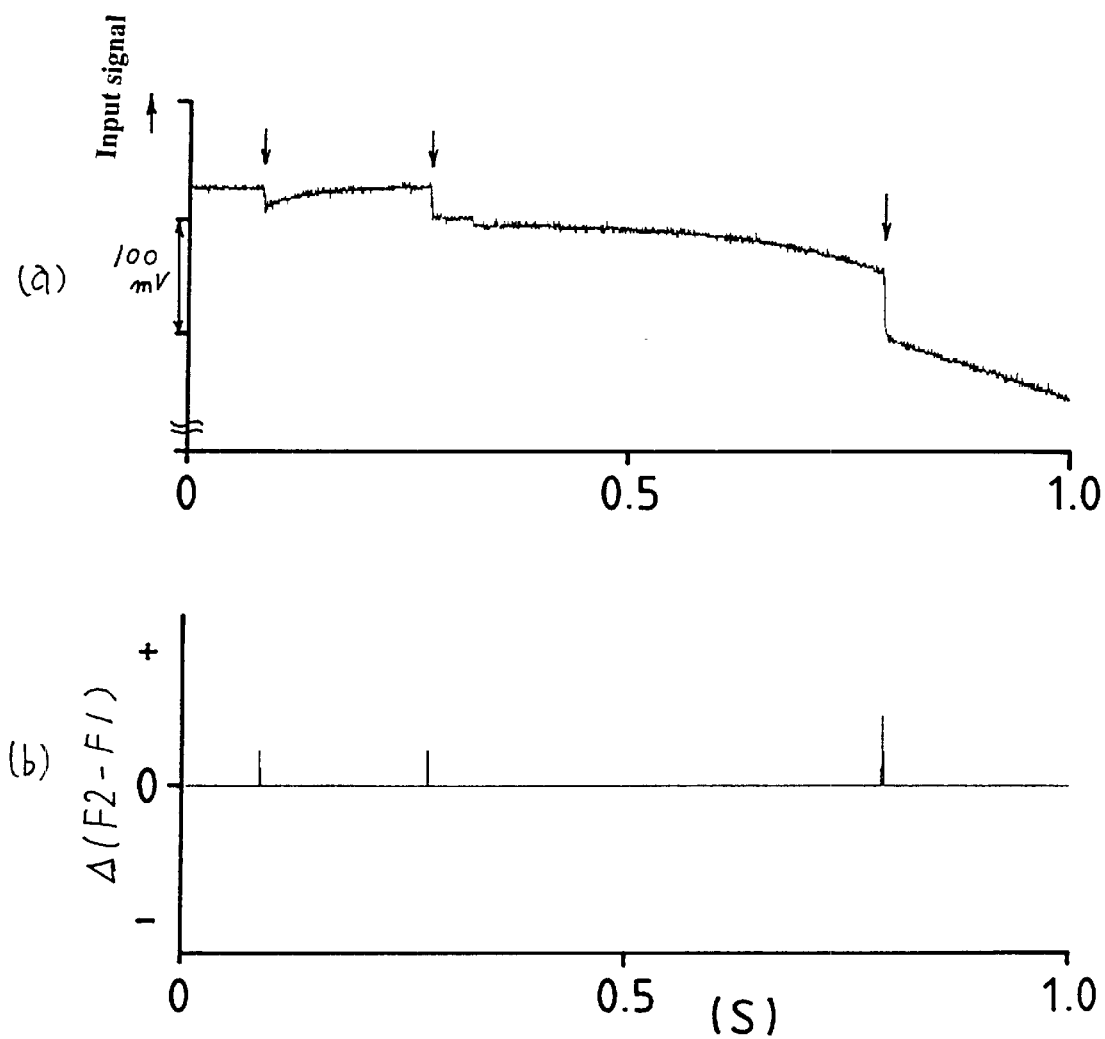
FIG. 9 is a schematic diagram showing the signal level of the photo detector and processed signal level when a fine rain drop impacts the sensing surface.
Figure 10:
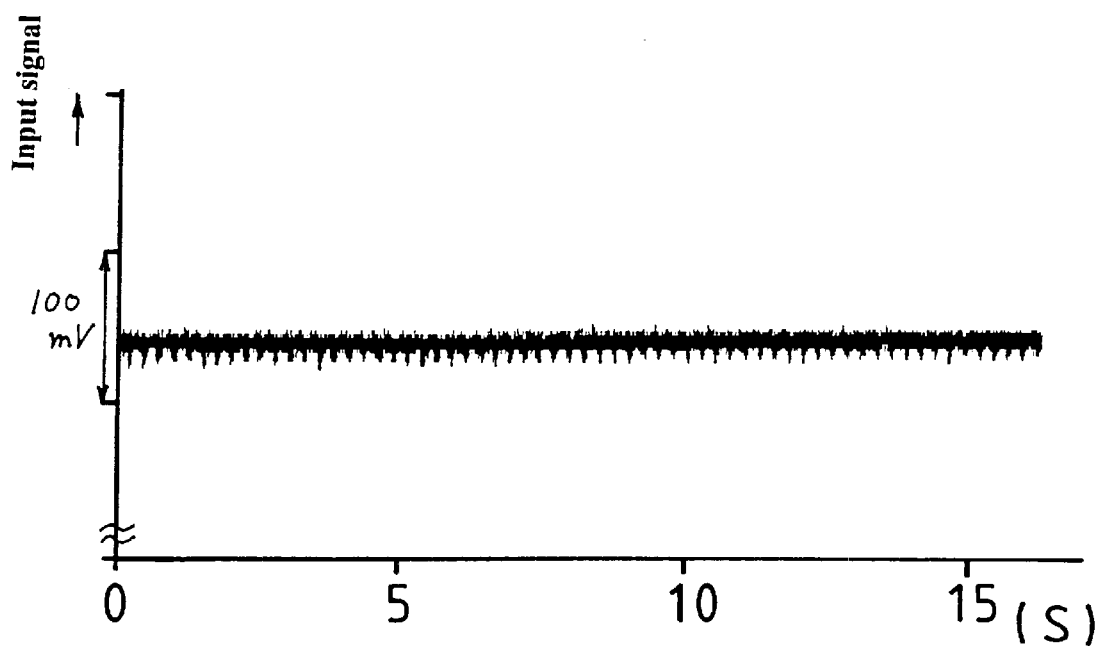
FIG. 10 is a schematic diagram showing the noise level included in the signal level of the photo detector used in this Embodiment 1.

Next, FIG. 9 shows the actual example of the signal when a small rain drop impacts the sensing surface. In FIG. 9, a rain drop impacts the sensing surface at the timing of the arrow (↓) shown in figure. The time base of the horizontal axis is different from that of FIG. 8. In addition, the noise level of this practical object sensor was about 25 mV as shown in FIG. 10. The amount of variation of the signal when a small rain drop impacted was about 23 mV or about 30 mV, and this level was not so much different from the noise level. However, it was able to be detected as a positive differential signal generated corresponding to the impact of the small rain drop.

[Counting Processing & Judging Processing]

The number of rain drops impacting the sensing surface sensed by the above mentioned method is counted by the counter, and the driving operation of the windshield wiper may be controlled according to the accumulation of the counted number (Refer to FIG. 6). The counted number can be reset by receiving every wiping signal indicating the instruction for wiping off the windshield.

Embodiment 2

Following is the description of the object sensor of Embodiment 2 of this invention. In Embodiment 2, another example of the hardware configuration of the object sensor of this invention that is different from that of FIG. 5 shown in Embodiment 1 is described. In the configuration shown in Embodiment 1, the analog signal inputted from the signal detection circuit 10 is converted into the digital signal by A/D conversion, and the noise canceling processing and/or the time lag signal generating processing were/was executed by the software processing means. In the configuration shown in this Embodiment 2, the analog signal inputted from the signal detection circuit 10 is used as an analog signal as it is, and the noise canceling processing and/or the time lag signal generating processing were/was executed by the analog circuit module generating the time lag signal. The optical system used in the object sensor of this Embodiment 2 can be the same optical system shown in FIG. 4 described in Embodiment 1, so that the description of the optical system used in this Embodiment 2 will be omitted here.

Figure 11:
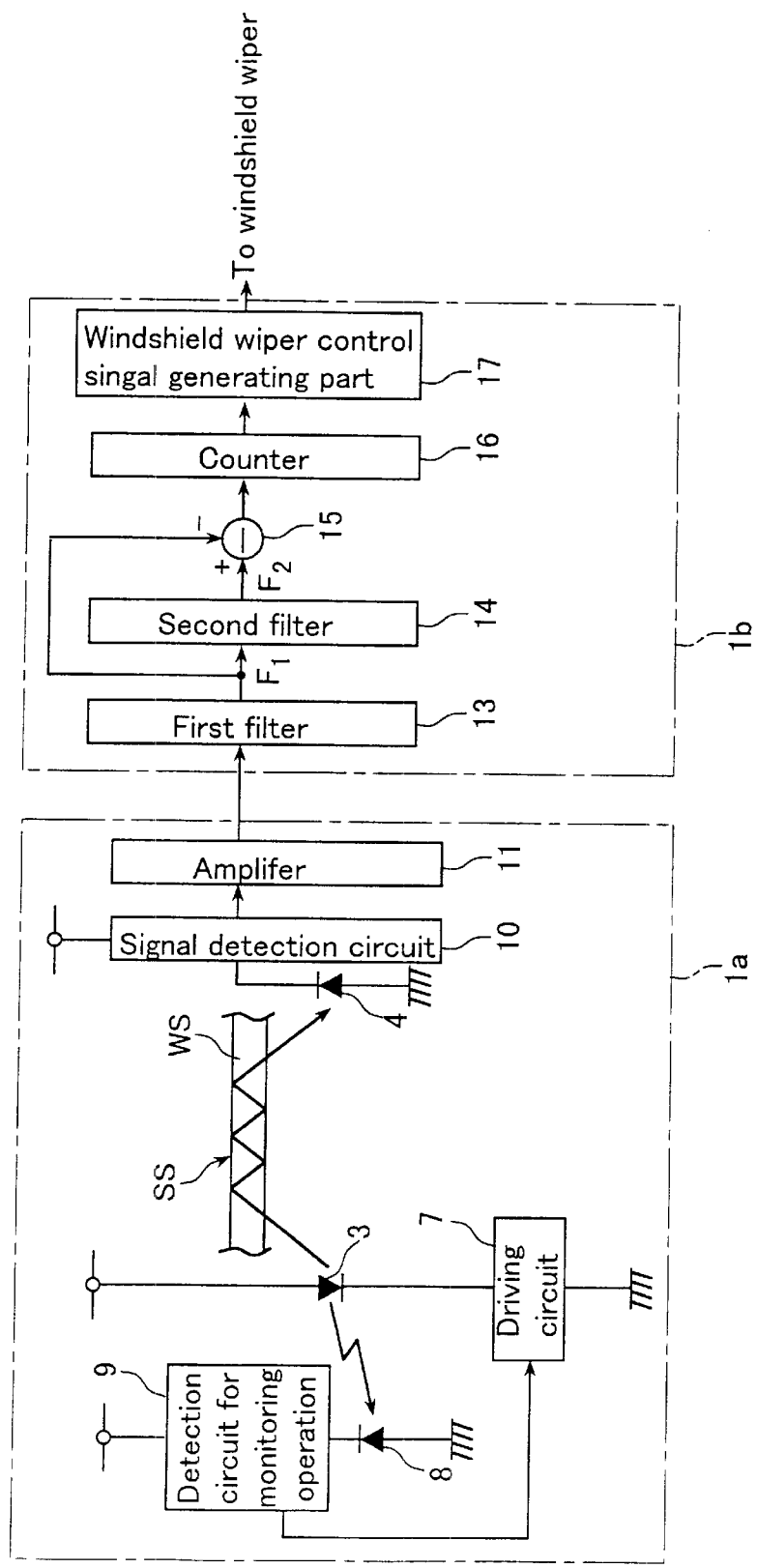
FIG. 11 is a block diagram showing the configuration of the hardware of the object sensor of Embodiment 2 of this invention.
Figure 12:
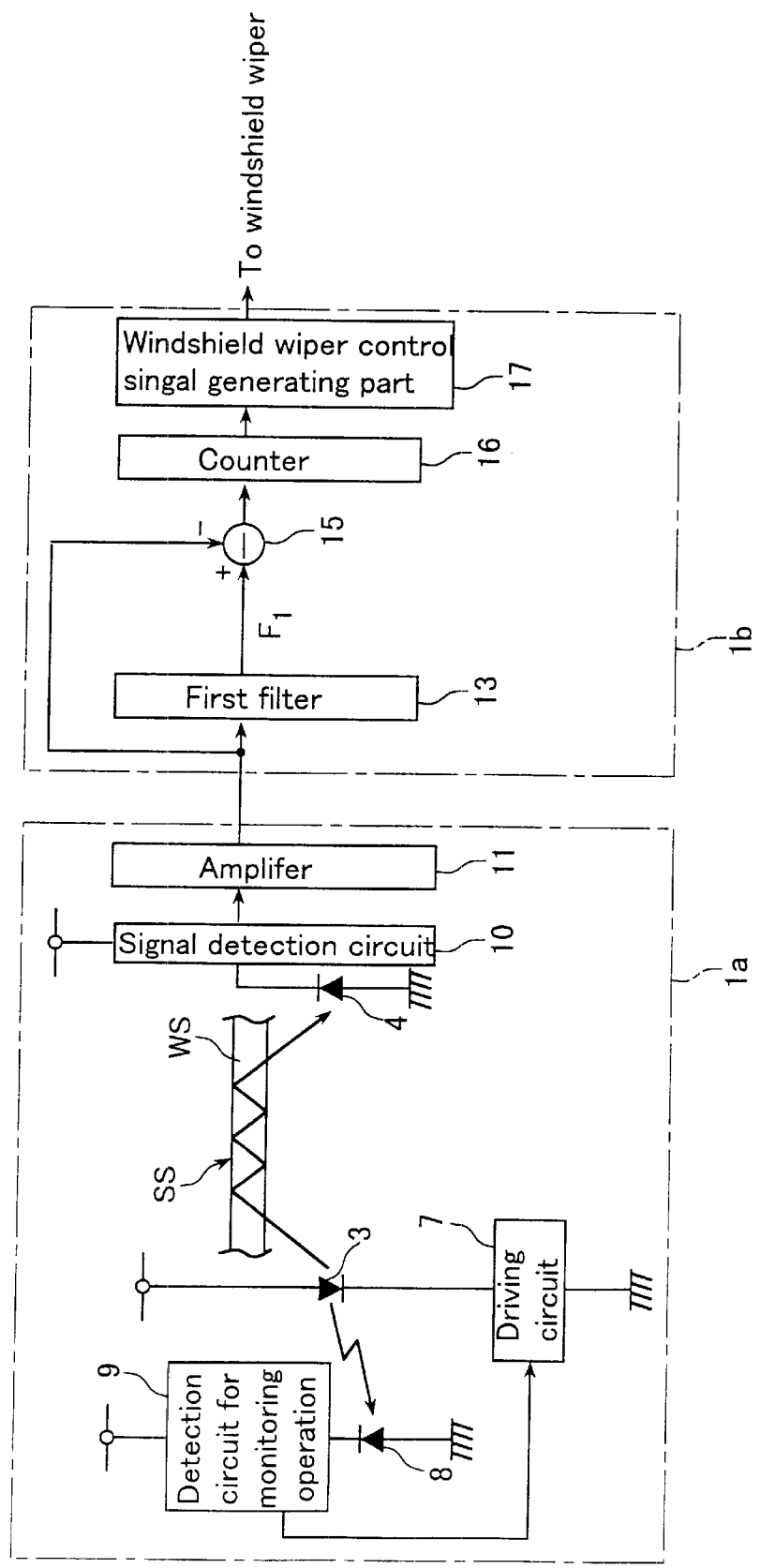
FIG. 12 is another block diagram showing the configuration of the hardware of the object sensor of Embodiment 2 of this invention.

FIG. 11 is a block diagram which shows the hardware of the object sensor of the Embodiment 2. In FIG. 11, the hardware circuit modules (1a) of a former section of the object sensor, the windshield (WS), the photo emission element (3), the photo detector (4), the driving circuit for photo emission element (7), the photo detector (9) for monitoring the operation, the signal detector (10), and the amplifier (11) can be similar respectively to the ones having the same element number of the circuit module of the former section in FIG. 5 shown in Embodiment 1. In FIG. 11, the hardware circuit modules (1b) of a latter section of the object sensor comprises the first filter (13), the second filter (14), the differential circuit (15), the counter circuit (16), and the windshield wiper control signal generation part (17).

The first filter (13) and the second filter (14) are the circuit modules for inputting the analog signal and outputting the processed analog signal after filtering, and these work as analog circuit modules for generating the time lag signal from the input signal. In FIG. 11, as an example, LC filters can be used as the first filter and the second filter, however, it is not limited to this example. Other examples such as RC filters can be another example as long as these can generate the time lag signal from the input signal. The relationship of the input signal and the output signal of the first filter (13) and the second filter (14) is the same as FIG. 3 and FIG. 8 shown in Embodiment 1, the output signal of the first filter (13) becomes F1 when the input signal is $D_{IN}$, and the output signal of the second filter (14) becomes F2 when the input signal is F1.

The differential circuit (15) has 2 input terminals, and it outputs the differential signal of the 2 input signals. When the configuration of the differential circuit is shown as FIG. 11, the output signal F1 of the first filter (13) and the output signal F2 of the second filter (14) are received as input signals and the differential signal $\Delta(F2-F1)$ is outputted. The Output signal $\Delta(F2-F1)$ of the differential circuit (15) becomes the same as the one shown in FIG. 3 and FIG. 8 described in Embodiment 1.

The counter (16) is a circuit that counts a positive differential signal appearing in the output signal $\Delta(F2-F1)$ of the subtractor (15). For instance, in the case of using the threshold method in the counting processing, the output signal $\Delta(F2-F1)$ of the subtractor (15) is inputted to the built-in comparator having a positive predetermined reference value as a threshold, and when the input signal value exceeds the threshold, the counted value is increased by one. The count value is outputted to the windshield wiper control signal generation part (17). The comparison processing with the threshold is included in the processing of the counter (16), but the counting processing by the threshold method can be performed correctly because the shift of the background and the noise are cancelled from the input signal.

The windshield wiper control signal generation part (17) is a control unit that receives the signal from the counter (16), generates the wiping off operation control signal of the windshield wiper according to the detected signal number or the detected signal frequency in the predetermined period and provides the generated operation control signal to the windshield wiper. The tuning of the control signal of the wiping off operation is possible. For instance, the control signal can be tuned as the signal for starting the wiper for the wiping off operation immediately according to the signal from the counter (16). In other cases, when the control signal is received the first time, the wiper does not perform wiping operation and when the control signal is received at the second time, the wiper performs wiping operation. Furthermore, the signal can be tuned as a signal for switching the wiping frequency according to the signal detection frequency in the predetermined period.

Figure 13:
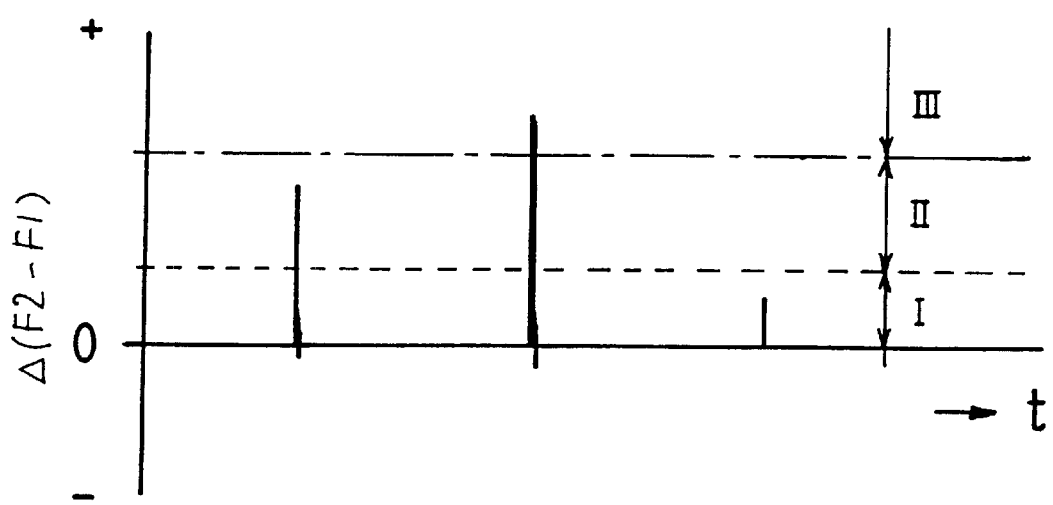
FIG. 13 is a schematic diagram showing a basic principle of the weighting of the difference by plural thresholds of Embodiment 3 of this invention.

In the above mentioned configuration, the first filter (13) and the second filter (14) are installed and the signals from these 2 filters are inputted to the subtractor (15). However, another configuration that uses only the first filter (13) and omits the second filter (14) as shown in FIG. 13 can be possible. In this case, the 2 input signals of the subtractor (15) will be the input signal $D_{IN}$ and the output signal F1 of the first filter (13). In this case, the output signal of the subtractor (15) becomes $\Delta(F1-D_{IN})$ as shown in FIG. 3(b). The counter (16) detects and counts a positive differential signal $\Delta(F1-D_{IN})$ as shown in FIG. 3(b).

Embodiment 3

In this Embodiment 3, the method and the apparatus for judging the status on the sensing surface by the size of the value of the differential signal are disclosed. In the object sensing method and apparatus of this invention, it is also possible to judge the status on the sensing surface according to the largeness of the value of the differential signal. For instance, because the size of the rain drop is not constant, the evaluation of sensing of a rain drop is weighted according to the size of the rain drop, the status of the windshield can be evaluated by the weighted value which can be regarded as the number of the rain drop or frequency of the rain drop. For instance, when a large-size rain drop impacts the sensing surface, a big differential signal will be generated by a rapid and big variation in the signal F1. It is confirmed in the practical experiment that the generated differential value corresponds to the size of the rain drop. Then, the weighting to the impact of an individual rain drop can be performed by setting plural different thresholds for the generated differential signal.

Figure 14:
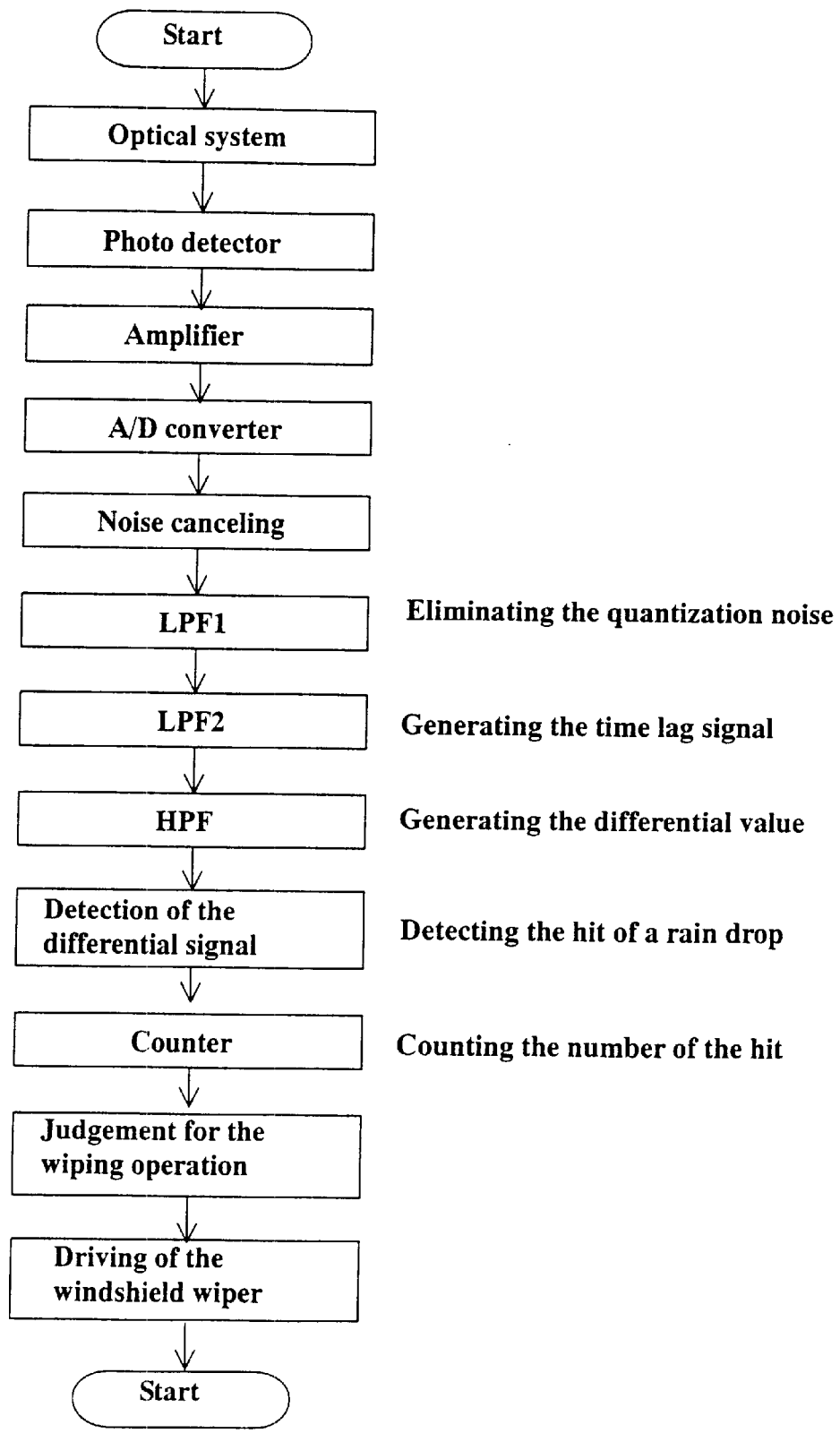
FIG. 14 is a flowchart showing the object sensing operations using weighting processing of this Embodiment 3.

FIG. 13 shows one example. As for the generated differential signal, the peak value is different according to the size of the impacting rain drop. Two thresholds are set here, and the rain drop is divided into three ranks (I,II,III). For weighting using this rank classification, the comparator having these two thresholds is used. The differential signal is inputted to the comparator. For instance, the weighting coefficient of rank I is assumed to be one, the weighting coefficient of the rank II is assumed to be two, and the weighting coefficient of the rank III is assumed to be three. The object sensor calculates the weighted value by multiplying the number of the differential signal by the above-mentioned weighting coefficient according to its rank, and accumulates those products while matching the timing of the differential signal detection. The example weighted value of total for FIG. 13 becomes 2+3+1=6. The weighting coefficient of each rank can be determined experimentally. The object sensor counts the weighted value obtained by the above mentioned calculation by using the counter, and the driving of the wiper can be controlled according to the accumulated number. FIG. 14 shows the flow chart of this processing.

Though the weighting evaluation mentioned shown above is processed by the comparison with the threshold, because the shift and the noise of the background are cancelled as for the input differential signal, the judgment by the threshold method can be performed correctly.

Embodiment 4

Embodiment 4 is an example of applying the object sensor of this invention to a windshield (WS) of a car. The object sensor applied here can be the object sensor explained in Embodiment 1, 2, or 3.

Figure 15:
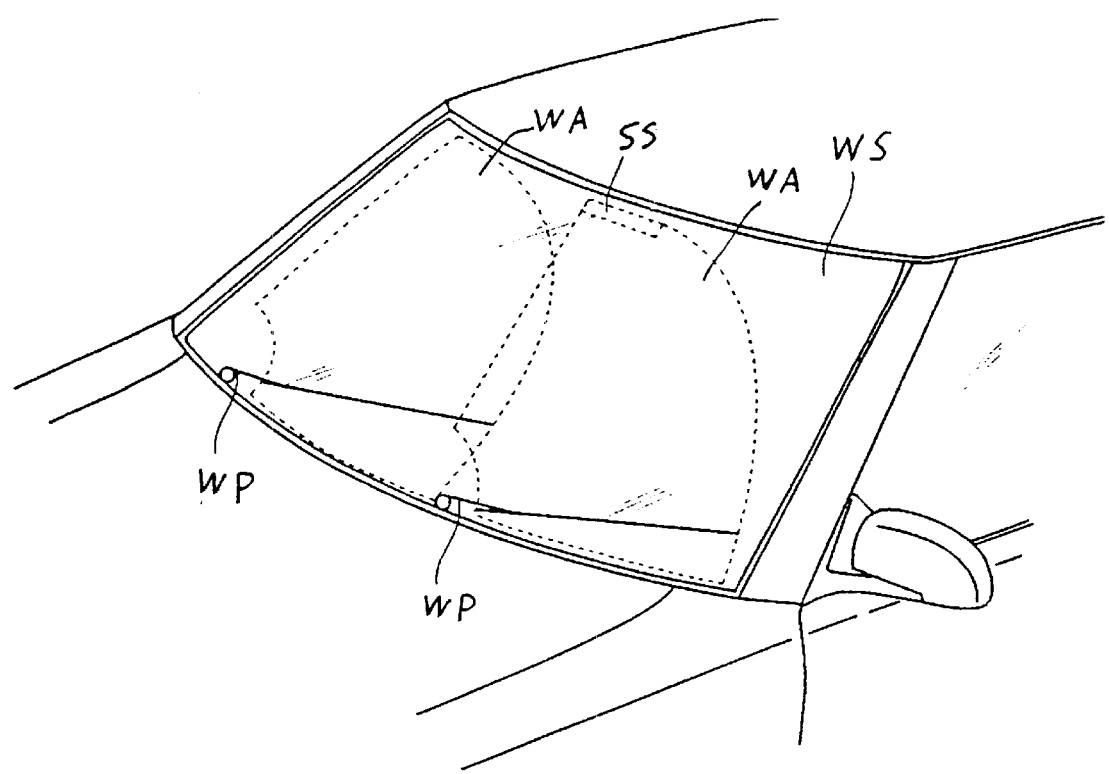
FIG. 15 is a schematic diagram showing the appearance where the object sensor of this invention is installed in a car.

FIG. 15 is a diagram showing the appearance where the object sensor of this invention is installed in a windshield of a car. The object sensor has been installed in the back of a rear view mirror (not shown in the figure) so as not to disturb driver's view. In addition, sensing surface (SS) of the object sensor is arranged within the range of wiping area of the wiper. The impact of the rain drop on the sensing surface (SS) of the object sensor is detected by the object sensor, then, for instance, the control signal from the wiper control signal generation part (17) shown in Embodiment 2 is supplied to the windshield wiper (WP), and the windshield wiper (WP) performs the wiping operation according to the control signal.

The invention of the object sensing method corresponding to the object sensing can be understood from the description of this specification.

That is, the method for canceling the noise and/or the method for generating the time lag signal are/is a sensing method for leveling a predetermined number of samples of the signal inputted one by one.

In the object sensing method of this invention, the object to be sensed for this sensing method is the impact of the water drop on the sensing surface.

In the object sensing method of this invention, the object to be sensed for this sensing method is the impact of the water drop on the sensing surface, and when the above-mentioned differential signal to be a value calculated by subtracting the signal of the photo detector from the above-mentioned time lag signal, or canceling the noise from the signal of the photo detector first, then subtracting it from the above-mentioned time lag signal, the object sensing method is a method for judging the impact of the water drop on the sensing surface when a positive differential signal is generated.

In the object sensing method of this invention, the object to be sensed for this sensing method is the impact of the water drop on the sensing surface, and when the above-mentioned differential signal is a value calculated by subtracting the first order time lag signal from the second order time lag signal, the object sensing method is a method for judging the impact of the water drop on the sensing surface when a positive differential signal is generated.

In the object sensing method of this invention, the object to be sensed for this sensing method is the impact of the rain drop on the sensing surface.

In the object sensing method of this invention, the size of the water drop can be judged by the differential value.

In the object sensing method of this invention, spike noises are cancelled from the signal of the photo detector.

In addition, the windshield wiper control method using the above mentioned object sensing method can be understood from the description of this specification.

It is understood that the above-mentioned object sensor and object sensing method can be modified in various configurations and the transformations without deviating the concept of the present invention. Therefore, this invention is not limited to the above-mentioned Embodiment.

As mentioned above, the object sensor of this invention provides the following effect.

The impact of the water drop on the sensing surface can be sensed because the object sensor can detect the status of the sensing surface by detecting the generation of the differential signal between the signal of the photo detector and the time lag signal.

This sensing processing can be performed by detecting only the generation of the differential signal, so that the sensing process can be performed by a simple logic.

Furthermore, the impact of an object such as a water drop on the sensing surface can be sensed adequately even if the signal level is fluctuated according to the temperature characteristic of the photo emission element and photo detector.

An adequate wiper operation control with few malfunctions becomes possible by controlling the driving of the wiper according to the output of the object sensor mentioned above.

Furthermore, the status on the sensing surface can be detected according to the differential signal value.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. An object sensor sensing the status of a sensing surface by detecting a light with a photo detector, which light has been emitted by a photo emission element and reflected on the sensing surface, comprising:

a means for generating a time lag signal from the output signal of the photo detector;

a means for calculating a differential signal between the output signal of the photo detector and the time lag signal; and a means for judging the status of the sensing surface by detecting the generation of the differential signal.

2. The object sensor according to claim 1, wherein said means for canceling the noise and/or said means for generating a time lag signal are/is an analog circuit for generating the time lag signal.

3. The object sensor according to claim 1, further comprising an A/D conversion means for converting an analog signal to a digital signal by sampling the analog signal of the photo detector over a predetermined period;

wherein said means for canceling the noise and/or said means for generating a time lag signal are/is a means for leveling the predetermined number of the sampled signal inputted sequentially from the A/D conversion means.

4. The object sensor according to claim 1, wherein said object to be sensed is an impact of a water drop on the sensing surface.

5. The object sensor according to claim 1, wherein said object to be sensed is an impact of a water drop on the sensing surface, and when the differential signal is calculated as a value by subtracting the signal of the photo detector or the signal of the noise-cancelled signal from the time lag signal, the impact of a water drop on the sensing surface is sensed when a positive differential signal is generated.

6. The object sensor according to claim 5, wherein said object to be sensed is an impact of a rain drop on the sensing surface.

7. The object sensor according to claim 6, wherein the size of the water drop impacting the sensing surface is judged by the value of the differential signal.

8. The object sensor according to claim 1, the spike noise is cancelled from the signal of the photo detector.

9. A windshield wiper control system that controls a windshield wiper by the signal outputted from the object sensor claimed in claim 1.

10. An object sensor sensing the status of a sensing surface by detecting a light with a photo detector, which light has been emitted by a photo emission element and reflected on the sensing surface, comprising:
- a means for canceling a noise in a signal outputted from a photo detector;
- a means for generating a time lag signal from the noise-cancelled signal;
- a means for calculating a differential signal between the noise-cancelled signal and the time lag signal; and
- a means for judging the status of the sensing surface by detecting the generation of the differential signal.

11. The object sensor according to claim 10, wherein said means for canceling the noise and/or said means for generating a time lag signal are/is an analog circuit for generating the time lag signal.

12. The object sensor according to claim 10, further comprising an A/D conversion means for converting an analog signal to a digital signal by sampling the analog signal of the photo detector over a predetermined period;
- wherein said means for canceling the noise and/or said means for generating a time lag signal are/is a means for leveling the predetermined number of the sampled signal inputted sequentially from the A/D conversion means.

13. The object sensor according to claim 10, wherein said object to be sensed is an impact of a water drop on the sensing surface.

14. The object sensor according to claim 10, wherein said object to be sensed is an impact of a water drop on the sensing surface, and when the differential signal is calculated as a value by subtracting the signal of the photo detector or the signal of the noise-cancelled signal from the time lag signal, the impact of a water drop on the sensing surface is sensed when a positive differential signal is generated.

15. The object sensor according to claim 14, wherein said object to be sensed is an impact of a rain drop on the sensing surface.

16. The object sensor according to claim 15, wherein the size of the water drop impacting the sensing surface is judged by the value of the differential signal.

17. The object sensor according to claim 10, the spike noise is cancelled from the signal of the photo detector.

18. A windshield wiper control system that controls a windshield wiper by the signal outputted from the object sensor claimed in claim 10.

19. An object sensor sensing the status of a sensing surface by detecting a light with a photo detector, which light has been emitted by a photo emission element and reflected on the sensing surface, comprising:
- a means for generating a first order time lag signal from the output signal of the photo detector;
- a means for generating a second order time lag signal from the first order time lag signal;
- a means for calculating a differential signal between the first order time lag signal and the second order time lag signal; and
- a means for judging the status of the sensing surface by detecting the generation of the differential signal.

20. The object sensor according to of claim 19, wherein said means for canceling the noise and/or said means for generating a time lag signal are/is an analog circuit for generating the time lag signal.

21. The object sensor according to claim 19, further comprising an A/D conversion means for converting an analog signal to a digital signal by sampling the analog signal of the photo detector over a predetermined period;
- wherein said means for canceling the noise and/or said means for generating a time lag signal are/is a means for leveling the predetermined number of the sampled signal inputted sequentially from the A/D conversion means.

22. The object sensor according to claim 19, wherein said object to be sensed is an impact of a water drop on the sensing surface.

23. The object sensor according to claim 19, wherein said object to be sensed is an impact of a water drop on the sensing surface, and when the differential signal is calculated as a value by subtracting the first order time lag signal from the second order time lag signal, the impact of a water drop on the sensing surface is sensed when a positive differential signal is generated.

24. The object sensor according to claim 23, wherein said object to be sensed is an impact of a rain drop on the sensing surface.

25. The object sensor according to claim 24, wherein the size of the water drop impacting the sensing surface is judged by the value of the differential signal.

26. The object sensor according to claim 19, the spike noise is cancelled from the signal of the photo detector.

27. A windshield wiper control system for controlling a windshield wiper by the signal outputted from the object sensor claimed in claim 19.

28. An object sensor sensing the status of a sensing surface by detecting a light with a photo detector, which light has been emitted by a photo emission element and reflected on the sensing surface, comprising:
- a circuit element for generating a time lag signal from the output signal of the photo detector;
- a circuit element for calculating a differential signal between the output signal of the photo detector and the time lag signal; and
- a circuit element for judging the status of the sensing surface by detecting the generation of the differential signal.

29. The object sensor according to claim 28, wherein said circuit element for canceling the noise and/or said circuit element for generating a time lag signal are/is an analog circuit for generating the time lag signal.

30. The object sensor according to claim 28, further comprising an A/D conversion circuit element for converting an analog signal to a digital signal by sampling the analog signal of the photo detector over a predetermined period;
- wherein said circuit element for canceling the noise and/or said circuit element for generating a time lag signal are/is a circuit element for leveling the predetermined number of the sampled signal inputted sequentially from the A/D conversion circuit element.

31. The object sensor according to claim 28, wherein said object to be sensed is an impact of a water drop on the sensing surface.

32. The object sensor according to claim 28, wherein said object to be sensed is an impact of a water drop on the sensing surface, and when the differential signal is calculated as a value by subtracting the signal of the photo detector or the signal of the noise-cancelled signal from the time lag signal, the impact of a water drop on the sensing surface is sensed when a positive differential signal is generated.

33. The object sensor according to claim 32, wherein said object to be sensed is an impact of a rain drop on the sensing surface.

34. The object sensor according to claim 33, wherein the size of the water drop impacting the sensing surface is judged by the value of the differential signal.

35. The object sensor according to claim 28, the spike noise is cancelled from the signal of the photo detector.

36. A windshield wiper control system that controls a windshield wiper by the signal outputted from the object sensor claimed in claim 28.

37. An object sensor sensing the status of a sensing surface by detecting a light with a photo detector, which light has been emitted by a photo emission element and reflected on the sensing surface, comprising:
a circuit element for canceling a noise in a signal which is outputted from a photo detector;
a circuit element for generating a time lag signal from the noise-cancelled signal;
a circuit element for calculating a differential signal between the noise-cancelled signal and the time lag signal; and
a circuit element for judging the status of the sensing surface by detecting the generation of the differential signal.

38. The object sensor according to claim 37, wherein said circuit element for canceling the noise and/or said circuit element for generating a time lag signal are/is an analog circuit for generating the time lag signal.

39. The object sensor according to claim 37, further comprising an A/D conversion circuit element for converting an analog signal to a digital signal by sampling the analog signal of the photo detector over a predetermined period;
wherein said circuit element for canceling the noise and/or said circuit element for generating a time lag signal are/is a circuit element for leveling the predetermined number of the sampled signal inputted sequentially from the A/D conversion circuit element.

40. The object sensor according to claim 37, wherein said object to be sensed is an impact of a water drop on the sensing surface.

41. The object sensor according to claim 37, wherein said object to be sensed is an impact of a water drop on the sensing surface, and when the differential signal is calculated as a value by subtracting the signal of the photo detector or the signal of the noise-cancelled signal from the time lag signal, the impact of a water drop on the sensing surface is sensed when a positive differential signal is generated.

42. The object sensor according to claim 40, wherein said object to be sensed is an impact of a rain drop on the sensing surface.

43. The object sensor according to claim 41, wherein the size of the water drop impacting the sensing surface is judged by the value of the differential signal.

44. The object sensor according to claim 37, the spike noise is cancelled from the signal of the photo detector.

45. A windshield wiper control system that controls a windshield wiper by the signal outputted from the object sensor claimed in claim 37.

46. An object sensor sensing the status of a sensing surface by detecting a light with a photo detector, which light has been emitted by a photo emission element and reflected on the sensing surface, comprising:
a circuit element for generating a first order time lag signal from the output signal of the photo detector;
a circuit element for generating a second order time lag signal from the first order time lag signal;
a circuit element for calculating a differential signal between the first order time lag signal and the second order time lag signal; and
a circuit element for judging the status of the sensing surface by detecting the generation of the differential signal.

47. The object sensor according to claim 46, wherein said circuit element for canceling the noise and/or said circuit element for generating a time lag signal are/is an analog circuit for generating the time lag signal.

48. The object sensor according to claim 46, further comprising an A/D conversion circuit element for converting an analog signal to a digital signal by sampling the analog signal of the photo detector over a predetermined period;
wherein said circuit element for canceling the noise and/or said circuit element for generating a time lag signal are/is a circuit element for leveling the predetermined number of the sampled signal inputted sequentially from the A/D conversion circuit element.

49. The object sensor according to claim 46, wherein said object to be sensed is an impact of a water drop on the sensing surface.

50. The object sensor according to claim 46, wherein said object to be sensed is an impact of a water drop on the sensing surface, and when the differential signal is calculated as a value by subtracting the first order time lag signal from the second order time lag signal, the impact of a water drop on the sensing surface is sensed when a positive differential signal is generated.

51. The object sensor according to claim 50, wherein said object to be sensed is an impact of a rain drop on the sensing surface.

52. The object sensor according to claim 51, wherein the size of the water drop impacting the sensing surface is judged by the value of the differential signal.

53. The object sensor according to claim 46, the spike noise is cancelled from the signal of the photo detector.

54. A windshield wiper control system that controls a windshield wiper by the signal outputted from the object sensor claimed in claim 46.

55. An object sensing method for sensing the status of a sensing surface by detecting a light with a photo detector, which light has been emitted by a photo emission element and reflected on the sensing surface, comprising:
generating a time lag signal from the output signal of the photo detector;
calculating a differential signal between the output signal of the photo detector and the time lag signal; and
judging the status of the sensing surface by detecting the generation of the differential signal.

56. A windshield wiper control method comprising controlling a windshield wiper with the detection of differential signal claimed in claim 55.

57. An object sensing method for sensing the status of a sensing surface by detecting a light with a photo detector, which light has been emitted by a photo emission element and reflected on the sensing surface, comprising:

canceling a noise in a signal which is outputted from a photo detector;

generating a time lag signal from the noise-cancelled signal;

calculating a differential signal between the noise-cancelled signal and the time lag signal; and judging the status of the sensing surface by detecting the generation of the differential signal.

58. A windshield wiper control method comprising controlling a windshield wiper with the detection of differential signal claimed in claim 57.

59. An object sensing method for sensing the status of a sensing surface by detecting a light with a photo detector, which light has been emitted by a photo emission element and reflected on the sensing surface comprising:

generating a first order time lag signal from the output signal of the photo detector;

generating a second order time lag signal from the first order time lag signal;

calculating a differential signal between the first order time lag signal and the second order time lag signal; and judging the status of the sensing surface by detecting the generation of the differential signal.

60. A windshield wiper control method comprising controlling a windshield wiper with the detection of differential signal claimed in claim 59.

* * * * *